(12) United States Patent
Gellman

(10) Patent No.: US 6,676,624 B2
(45) Date of Patent: Jan. 13, 2004

(54) DRAINAGE DEVICES AND METHODS

(75) Inventor: Barry N. Gellman, North Easton, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/028,208

(22) Filed: Dec. 20, 2001

(65) Prior Publication Data

US 2003/0120261 A1 Jun. 26, 2003

(51) Int. Cl.[7] ............................................... A61M 5/00
(52) U.S. Cl. ............................................. 604/8; 604/14
(58) Field of Search ..................... 604/8, 14, 246, 604/544, 128, DIG. 25

(56) References Cited

U.S. PATENT DOCUMENTS

| | | | |
|---|---|---|---|
| 4,334,327 A | * 6/1982 | Lyman et al. ............ 623/23.66 |
| 4,586,505 A | 5/1986 | Sisson et al. ................ 128/344 |
| 4,643,716 A | * 2/1987 | Drach ........................... 604/8 |
| 4,790,809 A | * 12/1988 | Kuntz ........................... 604/8 |
| 4,790,810 A | * 12/1988 | Pugh et al. .................... 604/8 |
| 4,820,298 A | 4/1989 | Leveen et al. .................. 623/1 |
| 5,336,163 A | 8/1994 | DeMane et al. ................ 602/46 |
| 5,494,029 A | 2/1996 | Lane et al. ............ 128/207.15 |
| 5,531,718 A | 7/1996 | Sachse et al. |
| 5,681,274 A | 10/1997 | Perkins et al. ................. 604/8 |
| 5,725,568 A | 3/1998 | Hastings ........................ 623/1 |
| 5,765,568 A | 6/1998 | Sweezer, Jr. et al. ........ 128/898 |
| 5,769,812 A | 6/1998 | Stevens et al. ................ 604/4 |
| 5,769,882 A | * 6/1998 | Fogarty et al. ............. 128/898 |
| 5,792,094 A | 8/1998 | Stevens et al. ................ 604/4 |
| 5,800,375 A | 9/1998 | Sweezer et al. ............... 604/4 |
| 5,814,006 A | * 9/1998 | Planz ........................... 604/8 |
| 5,882,345 A | 3/1999 | Yoon ........................... 604/264 |
| 5,885,238 A | 3/1999 | Stevens et al. ................. 604/4 |
| 5,911,710 A | 6/1999 | Barry et al. ................. 604/249 |
| 5,919,183 A | 7/1999 | Field ........................... 604/530 |
| 5,938,653 A | 8/1999 | Pepin ........................... 604/527 |
| 6,024,729 A | 2/2000 | Dehdashtian et al. ....... 604/256 |
| 6,123,689 A | 9/2000 | To et al. ...................... 604/256 |
| 6,126,633 A | 10/2000 | Kaji et al. ............... 604/95.04 |
| 6,228,068 B1 | 5/2001 | Yoon ........................... 604/246 |
| 2002/0120327 A1 | * 8/2002 | Cox et al. ................... 623/1.16 |

FOREIGN PATENT DOCUMENTS

| | | |
|---|---|---|
| EP | 0 265 207 A1 | 4/1988 |
| EP | 0 709 108 A2 | 5/1996 |
| EP | 0 808 611 A2 | 11/1997 |
| WO | WO 01 91668 A | 12/2001 |

OTHER PUBLICATIONS

International Search Report for International Patent Application No. PCT/US02/35802, dated Feb. 19, 2003, 5 pages.

* cited by examiner

Primary Examiner—Weilun Lo
Assistant Examiner—Michael Bogart
(74) Attorney, Agent, or Firm—Testa, Hurwitz & Thibeault, LLP (57) ABSTRACT

A ureteral drainage stent is designed to be placed in a patient's ureter and extend into a patient's bladder. An elongated tubular segment includes a distal retention structure for placement in the renal cavity, and a proximal retention structure constructed at least partly from a foam material and for placement in a urinary bladder. A central lumen connects at least one opening in the distal retention structure to the foam proximal retention structure. The foam proximal retention structure typically extends along at least a lower part of the ureter, across the ureteral-vesical junction, and into the bladder, to provide drainage through multiple networked channels.

21 Claims, 6 Drawing Sheets

DRAINAGE DEVICES AND METHODS

TECHNICAL FIELD

This invention generally relates to medical devices for drainage of fluids, and more specifically to ureteral stents.

BACKGROUND INFORMATION

Ureteral stents are used to assist urinary drainage from the kidney to the urinary bladder in patients with a ureteral obstruction or injury, or to protect the integrity of the ureter in a variety of surgical manipulations. Stents may be used to treat or avoid ureteral obstructions (such as ureteral stones or ureteral tumors) which disrupt the flow of urine from the kidneys to the bladder. Serious obstructions may cause urine to back up into the kidneys, threatening renal function. Ureteral stents may also be used after endoscopic inspection of the ureter to prevent obstruction of the ureter by swelling of the ureteral wall caused by the surgical procedure.

Ureteral stents typically are tubular in shape, terminating in two opposing ends: a kidney distal end and a bladder proximal end. One or both of the ends may be coiled in a pigtail or J-shape to prevent the upward and/or downward migration of the stent due, for example, to physiological movements. A kidney end coil resides within the lumen of the kidney, known as the renal pelvis, and is designed to prevent stent migration down the ureter and into the bladder. The bladder-end coil resides in the bladder and is designed to prevent stent migration upward toward the kidney. The bladder coil is also used to aid in retrieval and removal of the stent. Regions such as the trigone region in the bladder and the region of the ureter near the bladder known as the ureteral-vesical junction are particularly sensitive to irritation by foreign objects. Commonly used bladder-end coils contact and irritate the trigone region causing discomfort to the patient. Similarly, the proximal region of the stent contacts the ureteral-vesical junction causing irritation and discomfort to the patient particularly during voiding. Additionally, ureteral stents, particularly the portion positioned within the ureteral-vesical junction and inside the bladder, may produce adverse effects including blood in the urine, a continual urge to urinate, strangury, and flank pain accompanying reflux of urine up the stent (e.g., when voiding). Such effects occur as pressure within the bladder is transmitted to the kidney. In short, while providing drainage from the kidney to the bladder, stents may also cause or contribute to significant patient discomfort and serious medical problems.

SUMMARY OF THE INVENTION

The present invention relates to a ureteral stent that reduces patient discomfort and urine reflux. In particular, the invention relates to a foam segment, disposed at the proximal end of the stent, which reduces urine reflux and minimizes contact with the trigone region and ureteral-vesical junction. When the stent is placed within the urinary system of a patient, the foam segment is located within the ureteral-vesical junction, and also in the bladder itself. The foam segment, constructed from a soft and compressible open-cell or reticulated foam material, for example, minimizes the amount of irritation to the ureteral-vesical junction and the trigone region. Also, the foam segment, which is present within or blocks the opening of the stent lumen, partially occludes the stent lumen. This partial occlusion of the lumen prevents the rapid flow of urine through the stent to the kidney during urine reflux.

The foam segment also forms a proximal retention structure that is positioned in the urinary bladder when the stent is in use and functions to restrain the migration of the stent towards the kidney. The stent also includes a distal retention structure, which when the stent is installed in the patient, is generally located in the renal pelvis and functions to prevent the migration of the stent down the ureter into the urinary bladder.

In one aspect, the invention relates to a ureteral stent that includes an elongated member that defines a lumen extending therethrough, a distal retention structure that is defined by a distal region of the elongated member, and a foam segment that extends from a proximal end of the elongated member and is in fluid communication with the lumen.

In one embodiment, the foam segment includes a proximal retention structure. The proximal retention structure prevents the migration of the stent upward towards a kidney. In another embodiment, a distal portion of the foam segment is contained within the lumen of the elongated member. In yet another embodiment, a portion of the foam segment is attached to an outer surface of a proximal end of the elongated member. In further embodiments, the foam segment may include an open-cell foam, a reticulated foam, or a closed-cell foam.

In another embodiment, an outer dimension of the proximal retention structure that is substantially perpendicular to a longitudinal axis of the elongated member is larger than the diameter of the elongated member. A proximal retention structure with such an outer dimension prevents the proximal retention structure from entering into a ureter. In various embodiments, the proximal retention structure may include a funnel shape, a conical shape or a spherical shape, for example. In yet another embodiment, an outer dimension of the distal retention structure that is substantially perpendicular to a longitudinal axis of the elongated member is larger than the diameter of the elongated member. A distal retention structure with such an outer dimension prevents the distal retention structure from entering into a ureter. In one embodiment the distal retention structure includes a coiled shape.

In one embodiment, the elongated member of the ureteral stent includes an outer diameter ranging from about 6 to about 12 French. In another embodiment, the elongated member may include a biocompatible plastic.

In one embodiment of the invention, the foam segment further includes a coaxial member that defines a lumen extending therethrough. The coaxial member is fixed within the foam segment, by a bonding process, for example. In another embodiment, the foam segment of the ureteral stent defines a lumen extending therethrough.

In another aspect, the invention relates to a method for draining urine from a kidney. The method first requires providing a ureteral stent such as previously described. The stent is then inserted into a ureter of a patient. In one embodiment, the stent is positioned such that at least a portion of the distal retention structure resides within a kidney. In another embodiment, the stent is positioned such that at least a portion of the foam segment of the stent resides within a ureteral-vesical junction. In another embodiment, the foam segment includes a proximal retention structure. The proximal retention structure is positioned in the bladder thus preventing the migration of the proximal end of the stent out of a urinary bladder.

In another aspect, the invention relates to a method of positioning a ureteral stent within a patient. The method includes providing a ureteral stent as previously described.

The method then includes positioning the stent within a patient using a guide wire and a pusher. First, the stent is mounted over a guide wire already positioned within the body and then is pushed along the guide wire utilizing a pusher to locate the stent within the ureter of a patient. The shape of the pusher, particularly the distal end of the pusher, conforms to a shape of a proximal end of the ureteral stent. This allows the pusher to effectively transfer the necessary force to the proximal end of the stent to position the stent within the patient. Once the stent is properly located within patient, the guide wire is removed from the patient. The pusher may also be removed from the patient after the procedure.

In one embodiment, the method further includes inserting the guide wire into a urinary tract of the patient. The guide wire may be inserted into the urinary tract prior to inserting the stent into the urinary tract. In another embodiment, the method further includes positioning the distal retention structure within a kidney. The distal retention structure prevents the stent from migrating down the ureter and into the urinary bladder. In yet another embodiment, the foam segment of the stent includes a proximal retention structure, and the method further includes positioning the proximal retention structure in a urinary bladder. The proximal retention structure prevents the stent from migrating out of the bladder and up the ureter. In yet another embodiment, mounting the stent over a guide wire includes inserting the guide wire within a lumen of the elongated member.

The foregoing and other aspects, embodiments, features, and advantages of the invention will become apparent from the following description, figures, and claims.

BRIEF DESCRIPTION OF THE DRAWINGS

In the drawings, like reference characters generally refer to the same parts throughout the different views. Also, the drawings are not necessarily to scale, emphasis generally being placed upon illustrating the principles of the invention.

FIGS. 2A–D depict an embodiment of a proximal region of a ureteral stent of the invention in longitudinal cross-section in different configurations within the ureter and urinary bladder. FIG. 2A depicting a proximal retention structure distant from the ureteral-vesical junction, and FIG. 2B depicting the proximal retention structure flushed with the ureteral-vesical junction.

DESCRIPTION

This invention generally relates to a ureteral stent that, when positioned within a urinary tract of a patient, signifi-cantly reduces discomfort to the patient. The stent of the present invention includes an elongated member and an attached foam segment. The foam segment extends from a proximal end of the elongated member, and a distal retention structure exists at a distal region of the elongated segment.

The wall of the elongated member, including the distal retention structure, may be constructed of a biocompatible plastic such as but not limited to any of polyester, nylon based biocompatible polymers, polytetrafluoroethylene polymers, silicone polymers, polyurethane polymers, polyethylene polymers, and thermoplastic polymers, for example. The wall of the elongated member is of sufficient thickness to resist the pressure from the adjacent tissue caused by a tumor, peristalsis, or swelling, for example, that would collapse the ureter if not for the presence of the stent. In contrast to the trigone region and the ureteral-vesical junction, the renal pelvis and the majority of the ureter are relatively insensitive to irritation by the presence of foreign objects. This allows for the use of a relatively stiff plastic in regions of the stent, such as the elongated member and distal retention structure, that contact these relatively insensitive regions of the body.

The foam segment, which contacts the sensitive trigone region and ureteral-vesical junction, is constructed of a foam material that is highly compressible and flexible and generally reduces irritation caused by the stent on these areas. Additionally, to further reduce irritation, the foam segment may be shaped to minimize contact with the trigone region in the bladder, for example. The foam segment also minimizes patient discomfort by reducing urine reflux from the bladder to the renal pelvis, particularly during voiding of the bladder. During voiding, the ureteral orifice to the bladder constricts and closes to prevent urine from flowing up the ureter as the bladder compresses to force urine out of the bladder. When the stent is in place in the body, the foam segment traverses the ureteral orifice to the bladder and is generally located within the ureteral-vesical junction. Due to the high compressibility of the foam segment, the ureteral orifice can compress the region of the foam segment traversing the orifice and effectively block the flow of urine into the ureter.

In addition, the foam segment prevents urine reflux by obstructing the rapid passage of urine through the foam segment and into the elongated member of the stent. In contrast, a stent with an unobstructed lumen allows substantially free movement of urine from the bladder, through the elongated member of the stent and into the renal pelvis. In order for urine to flow through the stent of the present invention the urine must flow through the portion of the foam segment that resides within the lumen of the elongated member and the portion that blocks the lumen opening at the proximal end of the elongated member. The foam segment slows the flow of urine by forcing urine to filter through the network of small channels and passageways present in the structure of the foam. The foam segment provides adequate drainage of urine from the kidney to the bladder, to which urine generally flows at a slow rate by wicking or dripping, while acting as a barrier to the rapid flow of urine from the bladder to the kidney, which occurs during urine reflux.

Figure 1A:
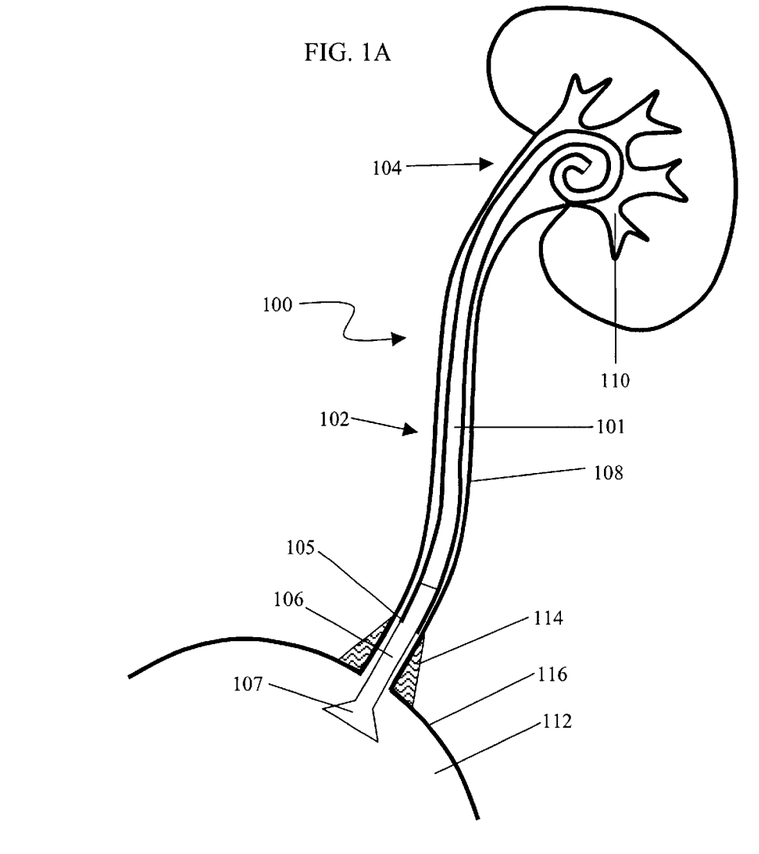
FIGS. 1A and 1B depict an embodiment of a ureteral stent of the invention, with FIG. 1A showing the device positioned in a ureter with a distal region in a kidney and a proximal region in a ureteral-vesical junction and bladder, and FIG. 1B showing the device outside of the body.
Figure 2A:
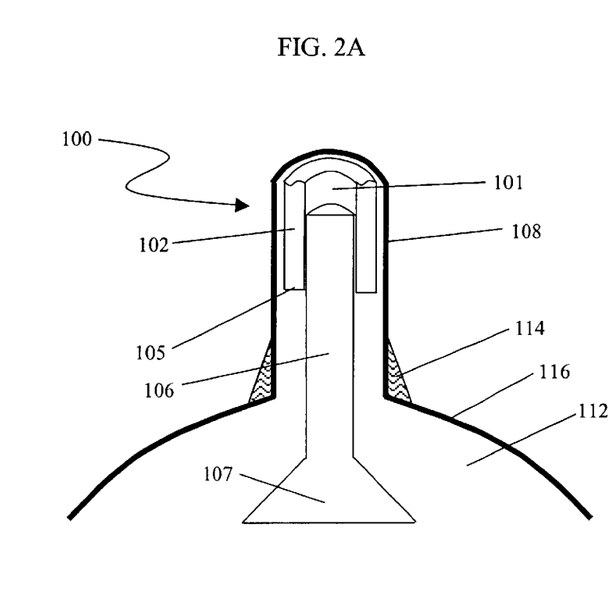
Figure 2B:
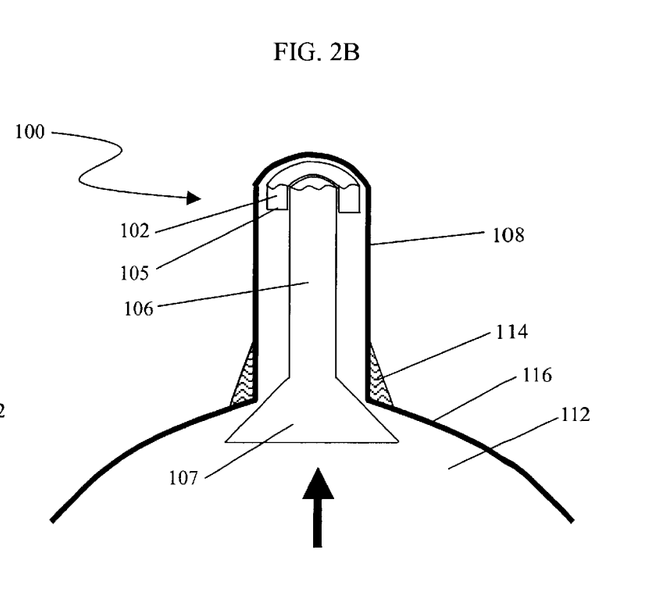

Referring to FIGS. 1A and 2B, a ureteral stent 100 includes an elongated member 102 defining a lumen 101. The stent 100 also includes a foam segment 106 extending from the proximal end 105 of the elongated member 102 and in fluid communication with the lumen 101 of the elongated member 102. The distal region of the elongated member 102 forms a distal retention structure 104. The elongated member 102 is generally located within the ureter 108 and the distal retention structure 104 is located in the renal pelvis 110. The foam segment 106 but not the elongated member 102 is located within the ureteral-vesical junction 114 and in the urinary bladder 112 when the stent 100 is properly positioned in the patient.

The stent 100 of the present invention minimizes patient discomfort by reducing the force and surface of contact between the stent 100 and the ureteral-vesical junction 114 and trigone region of the urinary bladder wall 116. The foam segment 106, which is more pliable, flexible, supple and compressible than the plastic tubing of elongated member 102, is the portion of the stent 100 that contacts these sensitive areas of the body. The foam segment 106 is less irritating or abrasive to the ureteral-vesical junction 114 and trigone region thus making the stent 100 more comfortable to the patient. However, the foam segment 106 is also sufficiently resilient to be shaped and formed as a proximal retention structure 107. The proximal retention structure 107 may be shaped to minimize contact with the trigone region and thus reduce the irritation caused by the contact.

Figure 1B:
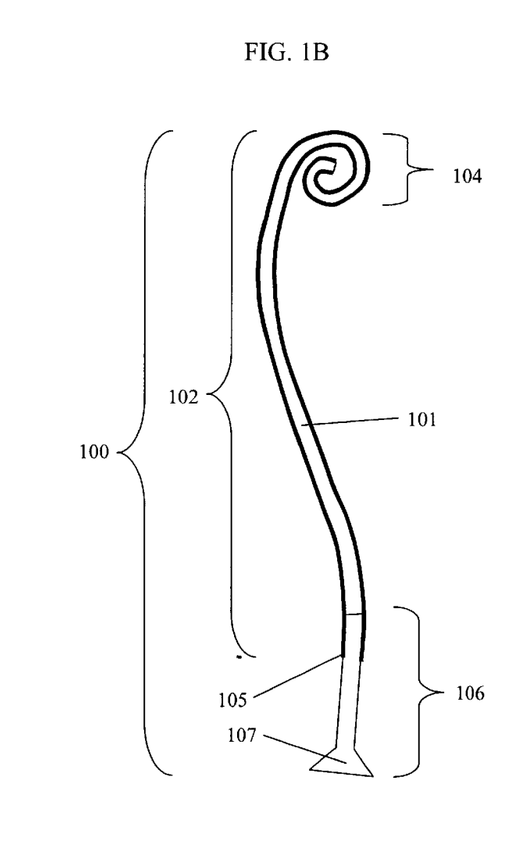

The stent 100 also minimizes patient discomfort by providing a barrier to urine flowing through the stent 100 from the bladder 112 into the renal pelvis 110. Urine must flow through the portion of the foam segment 106 that is present in the lumen 101. In FIG. 1B, the boundaries of the distal retention structure 104, elongated segment 102 and foam segment 106 are depicted. The length of overlap between the elongated segment 102 and foam segment 106 determines the amount of the foam segment 106 present inside the lumen 101. The amount of overlap may be varied depending on the density and type of the foam, the desired rate of urine flow through the stent 100, and the shape of the foam segment 106, for example. The foam segment 106, due to its high compressibility, lessens the resistance to the closing or constricting of the ureteral orifice to the bladder 112 during bladder voiding, and thus further assists in preventing urine reflux.

FIGS. 2A and 2B show schematic representation of the operation of the proximal retention structure 107 at the ureteral orifice. In FIG. 2A, the ureteral stent 100 is positioned in the patient so that the foam segment 106 and not the elongated segment 108 is within the ureteral-vesical junction 114. The foam segment 106, constructed from a compressible and flexible foam material, causes less irritation to the ureteral-vesical junction 114 than the elongated segment 108, which is constructed from a noncompressible and less flexible plastic material. In FIG. 2B, the ureteral stent 100 retracts towards the kidney and the proximal retention structure 107 of the foam segment 106 contacts the inner surface of the urinary bladder wall 116 preventing further movement of the ureteral stent 100 up the ureter 108 and towards the kidney. Movement of the ureteral stent 100 within the patient occurs by the expansion and contraction of the ureter caused by normal day-to-day activities of the patient. The proximal retention structure 107 and distal retention structure 104 maintain the stent 100 in the ureter 108 by restricting the movement of the stent 100 away from the urinary bladder 112 and kidney, respectively.

Figure 2C:
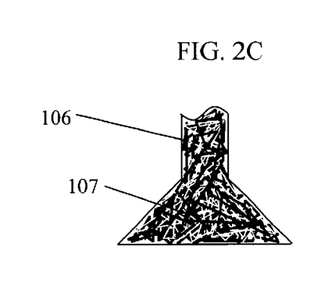
FIGS. 2C and 2D depicts the cross-sectional structure of reticulated and open-cell foam, respectively, that forms the foam segment and proximal retention structure.
Figure 2D:
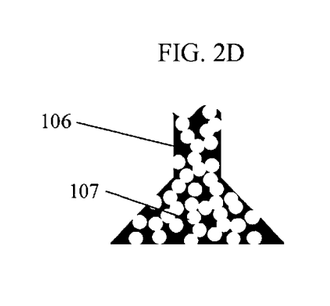

FIGS. 2C and 2D depict the microstructure of the reticulated and open-cell foam, respectively, that forms the foam segment 106. Both types of foam possess a structure that includes a plurality of curved and interconnecting passageways or channels that prevent the direct movement of urine through the foam segment 106. The structure of open-cell foam 106 (FIG. 2D) includes a plurality of cavities. The shape and size of the cavities may be fairly uniform or may vary. The cavities generally have one or more openings to one or more of the adjacent cavities. The arrangement of cavities produces foam that includes multiple passageways and channels that allows for the movement of liquids or gases therethrough. The multiple passageways and channels in reticulated foam 106 (FIG. 2C) are formed by the spaces created by a plurality of fibers bonded together in a network. The foam segment 106 located at least partially within and extending from the lumen 101 of the ureteral stent 100 slows the rate of fast or turbulent urine flow from retrograde pressure coming from the bladder 112 as it forces urine to travel through its plurality of small tortuous passageways. The foam segment 106, however, does not interfere with slow rates of urine flowing from the kidney into the bladder 112.

Referring to FIGS. 3A–D, embodiments of the present invention may further include a lumen 118 that extends through and may be oriented co-axially with the foam segment 106. The lumen 118 is in fluid communication with the lumen 101 of the elongated segment 102. The lumen 118 may be formed by removing a core of foam material from the foam segment 106. The lumen 118 increases the rate at which urine flows through the foam segment 106 by providing an unobstructed or large channel for urine to flow. The increased capacity for urine flow through the foam segment 106 increases the rate at which urine can flow through the stent 100 from the kidney to the bladder 112. However, the increased capacity for urine flow may be insufficient to allow substantial urine reflux. Urine reflux is further prevented in these embodiments by the collapsing of the surrounding flexible walls of the foam segment 106 that define the lumen 118. As the walls of the lumen 118 collapse, the cross-sectional area of the lumen 118 significantly decreases thus preventing a rapid flow of urine through the foam segment 106 and the stent 100.

Additionally, a coaxial member 120 that defines a lumen 118 may be inserted into the foam segment 106. The coaxial member 120 may be substantially tubular and may be bonded to the foam segment 106 fixing it in place. The coaxial member 120 reinforces the foam segment 106 by providing an embedded structural support of greater strength than the foam material alone. The coaxial member 120 may be of sufficient tensile strength to prevent the foam segment 106 from tearing during the grasping and pulling of the foam segment 106 during removal of the stent 100. More particularly, the coaxial member 120 may function to increase stiffness to the proximal retention structure 107 of the foam segment 106, in FIG. 3B for example. The coaxial member 120 may flare out on the surface of the proximal retention structure 107 thus conferring greater stiffness to the base of the cone-shaped portion of the proximal retention structure 107, in FIG. 3B for example. The lumen 118 defined by the foam segment 106 or the coaxial member 120 may function as a passageway for inserting a guide wire or cannula, for example, into the stent 100 during insertion, removal or repositioning of the stent in the body.

Embodiments of the foam segment 106 that include a lumen 118 (lumen 118 being defined either by the coaxial member 120 or the foam segment 106, for example) can be made of a closed-cell foam. The structure of closed-cell foam includes cavities or spaces in the material forming the foam, but the majority of the cavities or spaces are not interconnected, and the lack of interconnection between the cavities or spaces prevents the efficient flow of a liquid or gas through the closed-cell foam. When the foam segment 106 comprises closed-cell foam, it may not allow for sufficient drainage of urine through the stent 100 unless the lumen 118 is present in the foam segment 106 to allow for a sufficient flow of urine.

Figures 3A, 3B:
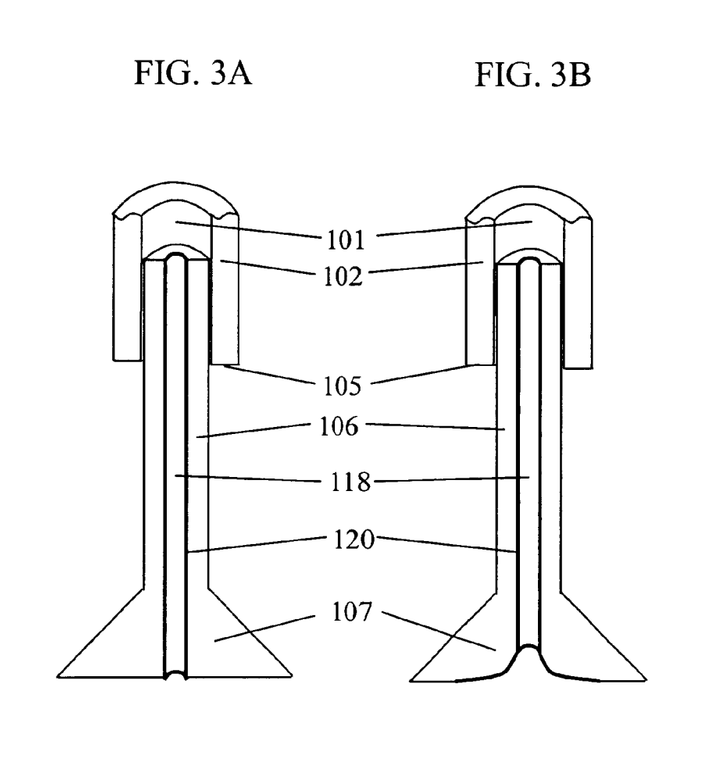
FIGS. 3A–D depict various embodiments of a proximal region of the ureteral stent of the invention in longitudinal cross-section.
Figures 3C, 3D:
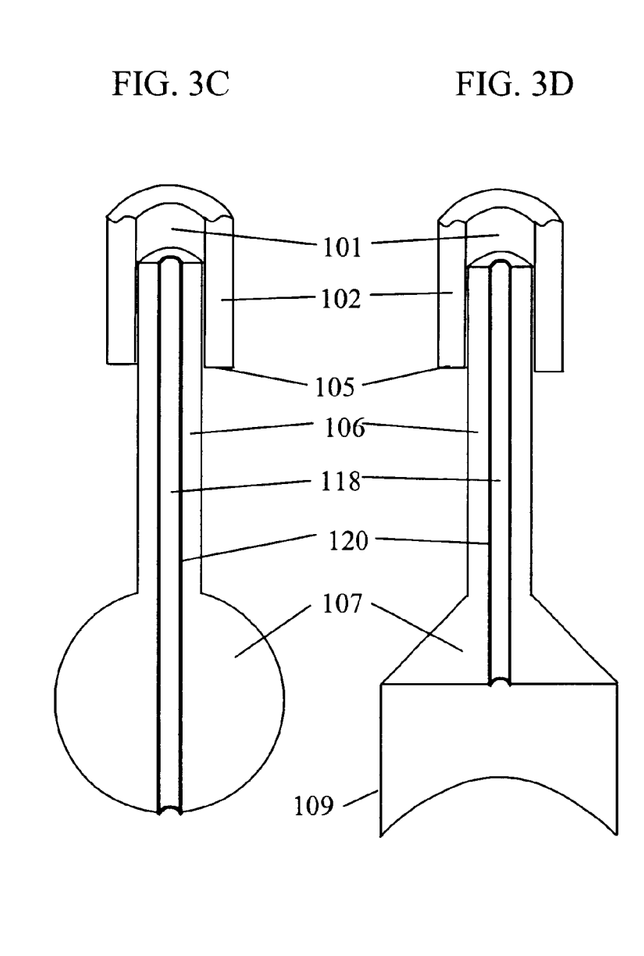

In FIGS. 3C and 3D, the proximal retention structure 107 may be in the shape of a sphere or a cone with a thin skirt 109 attached to the edge of the base of the cone. The foam segment 106 may be shaped in various ways to produce a proximal retention structure 107 that prevents the movement of the ureteral stent up the ureter 108 and minimizes or avoids contact with the trigone region.

Figure 4A:
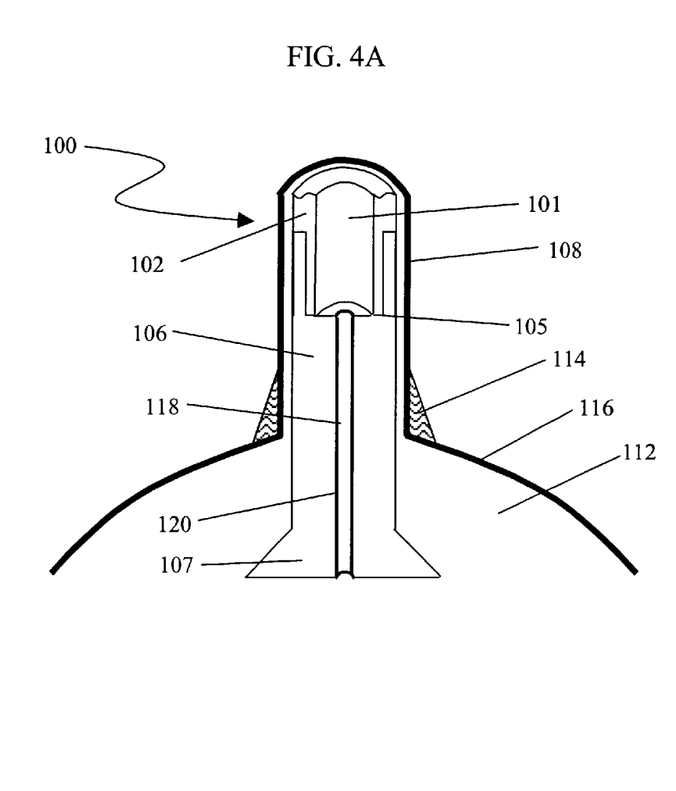
FIGS. 4A and 4B depicts other embodiments of a proximal region of a ureteral stent in longitudinal cross-section positioned in the ureter and urinary bladder.
Figure 4B:
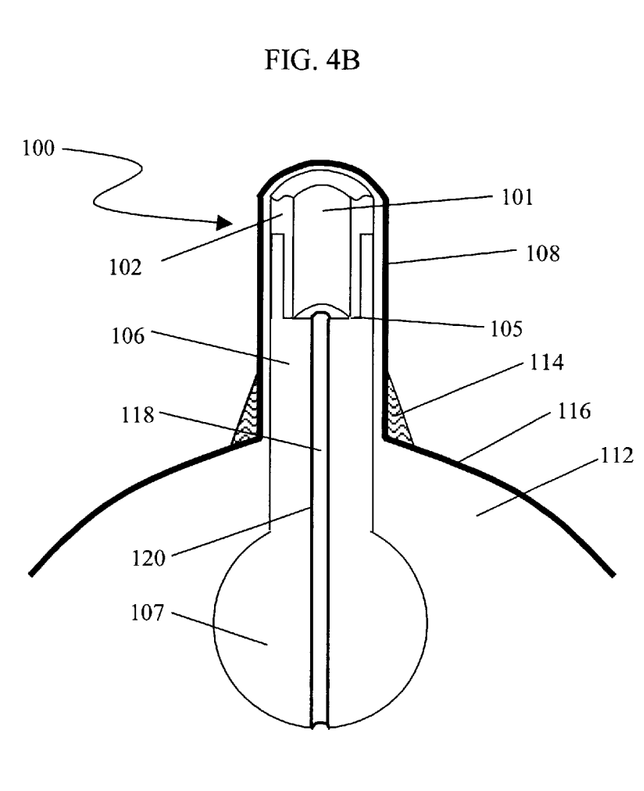

In FIGS. 4A–B, the foam segment 106 is fixed to the exterior surface of the elongated segment 102. In this embodiment, a portion of the foam segment 106 need not exist within the elongated segment 102. Additionally, the foam segment 106 may include a lumen 118. The lumen 118 may be defined by the foam segment 106 or by a coaxial member 120.

Figure 5A:
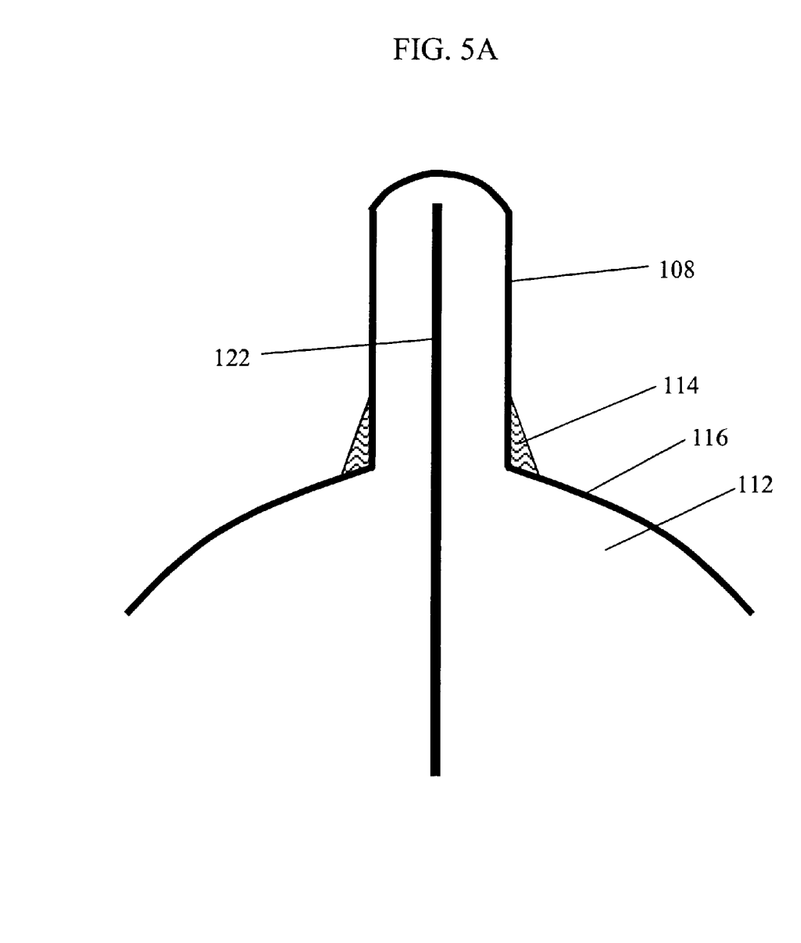
FIGS. 5A–D depict various steps involving a guide wire, a pusher and a ureteral stent in longitudinal cross-section positioned in the ureter and urinary bladder, as occurs during installation of the stent.
Figure 5B:
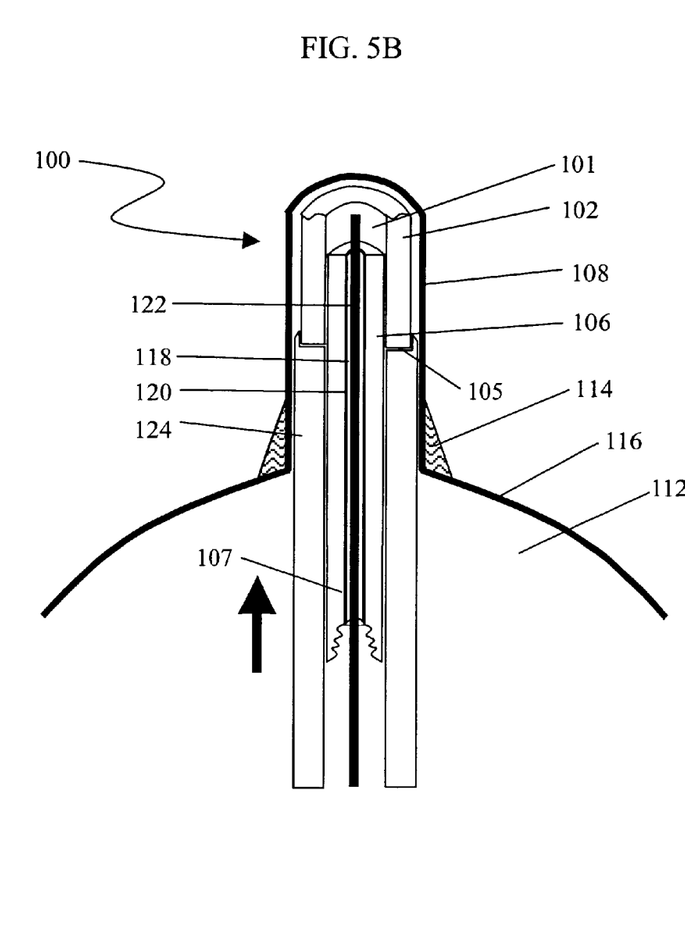

Referring to FIGS. 5A–D, the method of positioning a ureteral stent 100 within a patient is illustrated in a schematic with cross-sectional views of portions of the ureter 108 and urinary bladder 112. Draining urine from the kidney or ureter 108 may be accomplished by inserting a ureteral stent 100 according to the invention over a guide wire 122 with a pusher 124, through the urethra and urinary bladder 112 to the final position in the ureter 108. A guide wire 122 (FIGS. 5A and 5B) assists in the installation of the stent by providing a mechanical means of directing the stent 100 into the patient. The guide wire 122 is inserted into the body, through the urinary bladder 112 and ureter 108 until reaching the renal pelvis (FIG. 5A). Once the guide wire 122 is positioned in the patient, the stent 100 is inserted into the patient over the guide wire 122, which remains outside the body (FIG. 5B). The distal retention structure 104 is straightened as the guide wire is inserted through the lumen 101 and the stent 100 is moved along the length of the guide wire 122 and into the body with a pusher 124. In stent 100 embodiments that lack a lumen 118, alternative methods for passing the guide wire 122 through the foam segment 106 exist. The guide wire 122 may be passed through naturally occurring passageways or channels of the foam or through a channel formed by piercing the foam segment 106. The pusher 124 includes a lumen that is configured to accept a guide wire 122 and the proximal retention structure 107 (shown in a collapsed state in FIG. 5B). The guide wire 122 or a cannula may be used to temporarily straighten the distal retention structure.

Figure 5C:
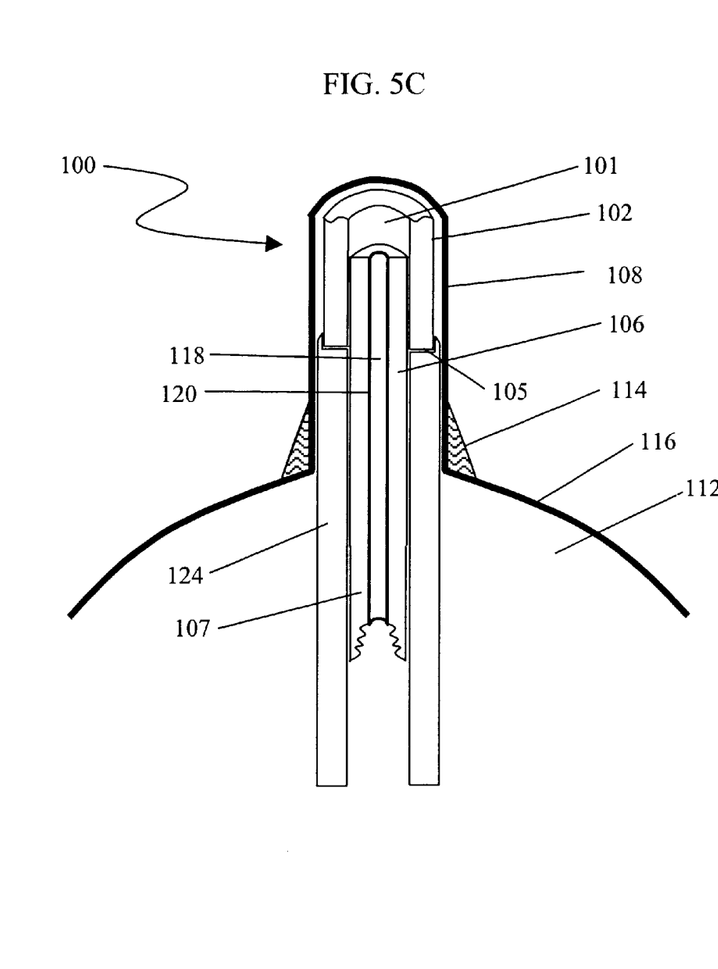

Once the ureteral stent 100 is properly positioned, the guide wire 122 may be removed (FIG. 5C). The distal retention structure is constructed from resilient material that regains its initial shape after distortion. The ureteral stent 100 may also be inserted into the patient by use of an endoscope, ureteroscope, or a cytoscope, for example.

Figure 5D:
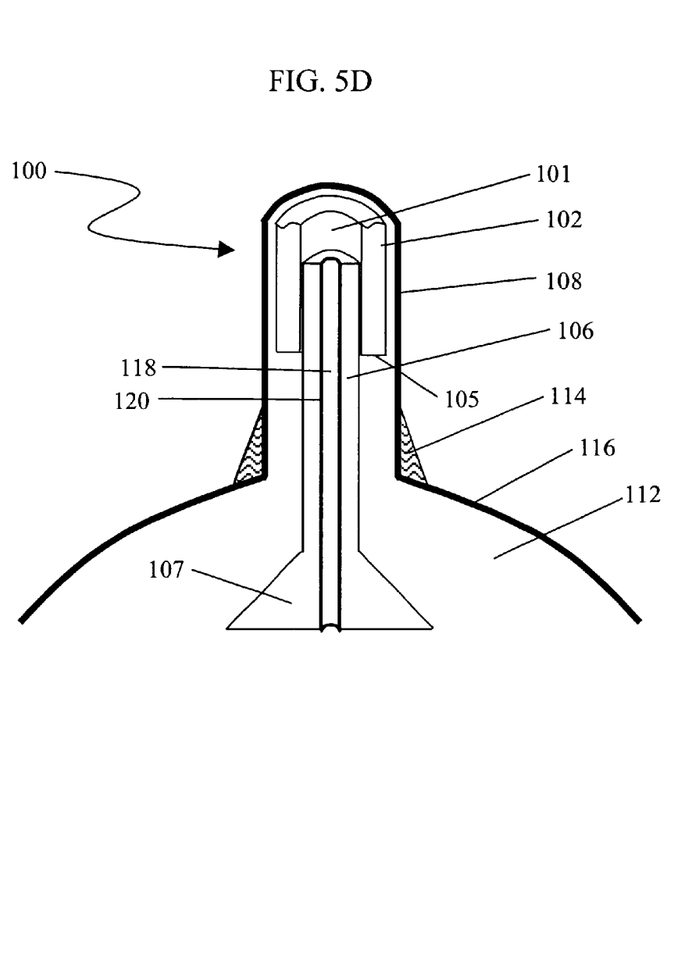

Once the stent 100 is positioned in the ureter 108, the pusher 124 may be withdrawn from the body of the patient (FIG. 5D). The ureteral stent 100 is positioned in the ureter 108 so that the distal retention structure is seated in the renal pelvis and the proximal retention structure 107 is located in the urinary bladder 112. Proper placement of the ureteral stent 100 positions the foam segment 106 within the ureteral-vesical junction 114 thus relieving irritation to this region and decreasing urine reflux.

Referring again to FIGS. 2A, 2B, 3A–D, 4A and 4B, the proximal retention structure 107 of the foam segment 106 may adopt a variety of shapes. Referring to FIGS. 5B and 5C, the pusher 124 abuts and applies a force against the proximal end 105 of the elongated segment 102 and the foam segment 106 to push the stent 100 into the body of the patient. To facilitate positioning of the stent 100 in the patient's body, the distal region of a pusher 124 conforms to the proximal end 105 of the elongated segment 102 and the foam segment 106. This allows for the force applied to the pusher 124 to be effectively transferred to the ureteral stent 100 during installation of the stent 100. Also, the lumen of the pusher 124 is large enough to house the foam segment 106 in a compressed state (FIGS. 5B and 5C). The lumen of the pusher 124 may include various inner diameters to conform to the various embodiments of the proximal retention structure 107 and foam segment 106.

Referring again to FIGS. 1A and 1B, the elongated member 102 is constructed by the extrusion of a biocompatible plastic such as but not limited to any of polyester, nylon based biocompatible polymers, polytetrafluoroethylene polymers, silicone polymers, polyurethane polymers, polyethylene polymers, and thermoplastic polymers, for example. The foam segment 106 may include reticulated foam (FIG. 2C), open-cell foam (FIG. 2D), closed-cell foam, and generally any material(s) that is/are functionally and/or structurally equivalent to the disclosed foams. The material (s) used to form the foam segment 106 may include urethane polymers, and one or more of the biocompatible plastics identified above in connection with the elongated member 102, and any generally similar material(s). The construction of the stent 100 includes bonding the foam segment 106 to the elongated member 102. The bonding of these two components may be performed by heat bonding. Heat bonding functions by partially melting the plastic on the surface of a structure, allowing the melted plastic to contact and adhere to a surface of another component, and allowing the plastic to cool and harden and thus form a bond. Heat bonding methods that include radio frequency bonding, induction heating and conduction heating may be used. The plastic of the foam segment 106 may be selected to melt at a similar temperature as the plastic of the elongated member 102 so that both components of the stent 100 are melted during the heat bonding process. Alternatively, either the foam segment 106 or elongated member 102 may be constructed from plastic with a lower melting temperature than the other component in order that only the component with the lower melting temperature melts during the bonding process.

Alternatively, the foam segment 106 and elongated member 102 may be bonded by the use of a bonding solvent, such as cyclohexanone and methylethylketone, for example. The bonding solvent acts by dissolving the plastic on the surface of the elongated member 102, for example. The foam segment 106 adheres to the dissolved plastic of the elongated member 102. The solvent may then be removed allowing for the dissolved plastic of the elongated member 102 to harden and thus complete the bonding process with the foam segment 106.

The bonding of the foam segment 106 to the elongated member 102 is facilitated by the use of a mandrel, for example. The bonding process includes the insertion of a mandrel into the foam segment 106, followed by the insertion of the foam segment 106 and mandrel into the elongated member 102. The mandrel compresses the foam segment 106 against the inner wall of the elongated member 102 thus facilitating the bonding of the two components. In embodiments of the invention in which the foam segment 106 is bonded to the outer wall of the elongated member 102 (FIGS. 4A and 4B), a pinching device may be used to compress the foam segment 106 against the outer wall of the elongated member 102 during the bonding process.

Embodiments of the foam segment 106 which include a coaxial member 120 (FIGS. 3A–3D, 4A and 4B) may be constructed by bonding the foam segment 106 to the elongated member 102 followed by inserting and bonding the coaxial member 120 in the foam segment 106. Alternatively, the coaxial member 120 may be inserted and bonded in the foam segment 106 prior to the insertion of the foam segment 106 into the elongated member 102. The coaxial member 120 may be bonded in the foam segment 106 by methods similar to those described for bonding the foam segment 106 to the elongated member 102.

Having thus described certain embodiments of the present invention, various alterations, modifications, and improvements will be apparent to those of ordinary skill. Such alterations, modifications, and improvements are intended to be within the spirit and scope of the invention. Accordingly, the foregoing description of embodiments of the invention is not intended to be limiting.

What is claimed is:

1. A ureteral stent comprising:
    an elongated member defining a lumen extending therethrough;
    a distal retention structure defined by a distal region of the elongated member; and
    a foam segment extending from a proximal end of the elongated member, and in fluid communication with the lumen, wherein a distal portion of the foam segment resides within the lumen.

2. The ureteral stent of claim 1, wherein the foam segment comprises a proximal retention structure.

3. The ureteral stent of claim 1, wherein the foam segment is attached to an outer surface of a proximal end of the elongated member.

4. The ureteral stent of claim 1, wherein the foam segment comprises at least one of an open-cell foam, a reticulated foam, or a closed-cell foam.

5. The ureteral stent of claim 1, wherein the foam segment comprises reticulated foam.

6. The ureteral stent of claim 1, wherein the foam segment comprises a closed-cell foam.

7. The ureteral stent of claim 2, wherein an outer dimension of the proximal retention structure substantially perpendicular to a longitudinal axis of the elongated member is larger than the diameter of the elongated member.

8. The ureteral stent of claim 2, wherein the proximal retention structure comprises at least one of a funnel shape, a conical shape, or a spherical shape.

9. The ureteral stent of claim 2, wherein the proximal retention structure comprises a conical shape.

10. The ureteral stent of claim 2, wherein the proximal retention structure comprises a spherical shape.

11. The ureteral stent of claim 1, wherein an outer dimension of the distal retention structure substantially perpendicular to a longitudinal axis of the elongated member is larger than the diameter of the elongated member.

12. The ureteral stent of claim 1, wherein the foam segment further comprises a coaxial member defining a lumen extending therethrough, the coaxial member fixed within the foam segment.

13. The ureteral stent of claim 1, wherein the foam segment defines a lumen extending therethrough.

14. A method for draining urine from a kidney, the method comprising the steps of:
    a) providing a ureteral stent comprising:
        an elongated member defining a lumen extending therethrough;
        a distal retention structure defined by a distal region of the elongated member; and
        a foam segment extending from a proximal end of the elongated member, and in fluid communication with the lumen;
    b) inserting said ureteral stent into a ureter of a patient; and
    c) positioning at least a portion of the foam segment of the stent in a ureteral-vesical junction.

15. The method of claim 14, further comprising the step of positioning at least a portion of the distal retention structure within a kidney.

16. The method of claim 14, wherein the foam segment comprises a proximal retention structure.

17. A method of positioning a ureteral stent within a patient, comprising the steps of:
    a) providing a ureteral stent comprising:
        an elongated member defining a lumen extending therethrough;
        a distal retention structure defined by a distal region of the elongated member; and
        a foam segment extending from a proximal end of the elongated member, and in fluid communication with the lumen; and
    b) mounting the stent over a guide wire;
    c) locating the ureteral stent within the ureter of a patient utilizing a pusher, wherein a shape of the pusher conforms to a shape of a proximal end of the ureteral stent; and
    d) removing the guide wire.

18. The method of claim 17, further comprising the step of inserting the guide wire within a urinary tract.

19. The method of claim 17, further comprising the step of positioning the distal retention structure within a kidney.

20. The method of claim 17, wherein the foam segment comprises a proximal retention structure and further comprising the step of positioning the proximal retention structure in a urinary bladder.

21. The method of claim 17, wherein mounting the stent over a guide wire comprises inserting the guide wire within a lumen of the elongated member.

* * * * *